(12) United States Patent
Karanam et al.

(10) Patent No.: US 11,475,997 B2
(45) Date of Patent: Oct. 18, 2022

(54) SYSTEMS AND METHODS FOR AUTOMATED HEALTHCARE SERVICES

(71) Applicant: SHANGHAI UNITED IMAGING INTELLIGENCE CO., LTD., Shanghai (CN)

(72) Inventors: Srikrishna Karanam, Brighton, MA (US); Yimo Guo, Lexington, MA (US); Ziyan Wu, Lexington, MA (US)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 289 days.

(21) Appl. No.: 16/798,100

(22) Filed: Feb. 21, 2020

(65) Prior Publication Data

US 2021/0265057 A1  Aug. 26, 2021

(51) Int. Cl.
*G16H 50/20* (2018.01)
*G16H 40/67* (2018.01)
(Continued)

(52) U.S. Cl.
CPC .......... *G16H 50/20* (2018.01); *A61B 6/0487* (2020.08); *A61B 6/5205* (2013.01);
(Continued)

(58) Field of Classification Search
CPC ........ G16H 50/50; G16H 50/30; G16H 30/40; G16H 20/40; G16H 40/63; G16H 50/20;
(Continued)

(56) References Cited

U.S. PATENT DOCUMENTS

2016/0113592 A1   4/2016 Murugappan et al.
2016/0278731 A1*  9/2016 Babic ................. A61B 5/0035
(Continued)

FOREIGN PATENT DOCUMENTS

CN   104582624 A   4/2015
CN   106845120 A   6/2017
(Continued)

OTHER PUBLICATIONS

Fattori, Giovanni, et al. "Automated fiducial localization in CT images based on surface processing and geometrical prior knowledge for radiotherapy applications." IEEE transactions on biomedical engineering 59.8 (2012): 2191-2199. (Year: 2012).*
(Continued)

*Primary Examiner* — Linh Giang Le
*Assistant Examiner* — Constantine Siozopoulos
(74) *Attorney, Agent, or Firm* — Zhong Law, LLC

(57) ABSTRACT

Healthcare services can be automated utilizing a system that recognizes at least one characteristic of a patient based on images of the patient acquired by an image capturing device. Relying on information extracted from these images, the system may automate multiple aspects of a medical procedure such as patient identification and verification, positioning, diagnosis and/or treatment planning using artificial intelligence or machine learning techniques. By automating these operations, healthcare services can be provided remotely and/or with minimum physical contact between the patient and a medical professional.

20 Claims, 4 Drawing Sheets

(51) Int. Cl.
  *G16H 80/00* (2018.01)
  *A61B 6/00* (2006.01)
  *A61B 6/04* (2006.01)

(52) U.S. Cl.
  CPC ............ *A61B 6/5294* (2013.01); *A61B 6/545* (2013.01); *G16H 40/67* (2018.01); *G16H 80/00* (2018.01)

(58) Field of Classification Search
  CPC ........ G16H 30/20; G16H 10/65; G16H 20/30; G16H 40/20; G16H 40/40; G16H 50/70
  See application file for complete search history.

(56) References Cited

U.S. PATENT DOCUMENTS

2017/0354385 A1* 12/2017 Lerch ................... A61B 6/4441
2019/0362137 A1  11/2019 Wang et al.
2019/0365498 A1* 12/2019 Gibby ................. A61B 5/1072

FOREIGN PATENT DOCUMENTS

WO         2012111013 A      8/2012
WO    WO-2017172641 A1 * 10/2017   ........... A61B 6/0492
WO    WO-2021141617 A1 *  7/2021   ............... G06N 3/08

OTHER PUBLICATIONS

International Application No. PCT/CN2020/131776, International Search Report and Written Opinion dated Mar. 2, 2021, 8 pages.
Cootes et al., "Active Shape Models—Their Training and Application," Computer Vision and Image Understanding, vol. 61, No. 1, 1995, pp. 38-59.
Ronneberger et al., "U-Net: Convolutional Networks for Biomedical Image Segmentation," arXiv:1505.4597v1, 2015, pp. 1-8.
Cootes et al., "Active Appearance Models," IEEE Transactions on Pattern Analysis and Machine Intelligence, vol. 23, No. 6, 2001, pp. 681-685.

* cited by examiner

SYSTEMS AND METHODS FOR AUTOMATED HEALTHCARE SERVICES

BACKGROUND

Conventional healthcare services generally require close contact between a patient and a medical professional. In radiation therapy and medical imaging, for instance, a doctor or technician usually needs to be present in the treatment room during at least the positioning stage to ensure that the patient get into a desirable position or pose to allow the treatment or scan to proceed in a precise and accurate manner. These traditional methods of providing healthcare services are manual in nature and suffer from human errors, inconsistencies and lack of real-time monitoring capabilities. At the same time, close contact between patients and medical professionals may lead to increased risks of cross-contamination, unintended exposure to radiation, and/or violent incidents ranging from verbal abuse to physical assaults.

SUMMARY

Described herein are systems, methods and instrumentalities for providing automated (e.g., remote and/or contactless) healthcare services to a patient. In an example implementation, an automated healthcare system may include a sensing or image capturing device installed in a medical environment and configured to capture images of a patient. The images may be transmitted to or retrieved by a control unit and used to determine at least one characteristic of the patient. In examples, the physical characteristics and/or identity of the patient may be determined by analyzing the images (e.g., at a pixel level) using artificial intelligence methods and/or machine-learned models. Relying on the identity and/or the at least one characteristic of the patient determined via such methods or models, the control unit may automatically complete one or more aspects of a medical procedure for the patient, for example, remotely and/or without requiring close human contact with the patient. In examples, the automated aspects may include remotely controlling a medical device or remotely providing instructions (e.g., positioning instructions) to the patient in connection with the medical procedure based on the characteristic of the patient extracted from the images of the patient. In examples, the automated aspects may include determining the readiness of the patient for the medical procedure and/or movements of the patient before and during the medical procedure based on the images collected by the image capturing device. In examples, the automated aspects may include determining a spatial relationship between the image capturing device and a medical device (e.g., a medical scanner) and complete one or more aspects of the medical procedure based on the spatial relationship. For example, the spatial relationship may be used to determine a parameter (e.g., a scan parameter) associated with the medical procedure and the one or more images of the patient may be overlaid with an indication of the parameter to facilitate decision making. In examples, the automated aspects may also include providing instructions to the patient or feedback to a medical professional (e.g., located remotely from the patient) regarding the status of the patient or the progression of the medical procedure.

The images of the patient described herein may include photos of the patient taken by a camera or thermal images of the patient generated by a thermal sensor. The at least one characteristic of the patient determined from these images may include the height, weight, and/or body shape of the patient. In addition, the automation of the medical procedure may be further assisted by patient information retrieved from other sources including, for example, a medical record repository. Such information may be used to verify the identity of the patient and/or to automatically determine the protocols or parameters associated with the medical procedure.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
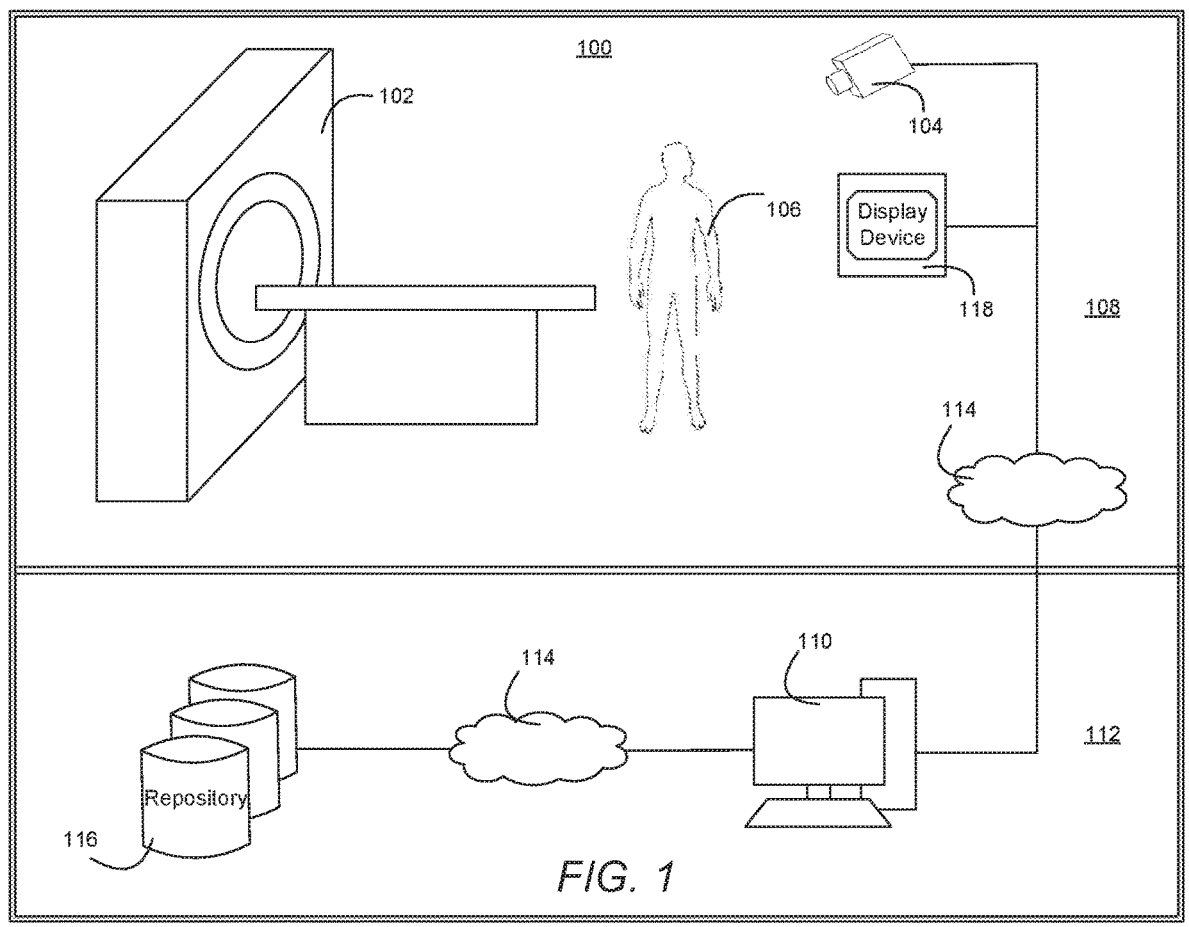
FIG. 1 is a simplified diagram illustrating an example system for providing automated healthcare services as described herein.

FIG. 1 is a diagram illustrating an example system 100 for providing automated healthcare services at a medical facility such as a hospital. The healthcare services may include, for example, a medical scan procedure conducted via a medical scanner 102 (e.g., a computer tomography (CT) scanner, a magnetic resonance imaging (MRI) machine, a positron emission tomography (PET) scanner, an X-ray machine, etc.), or a radiation treatment procedure delivered through a medical linear accelerator (LINAC) (not shown). One or more aspects of the healthcare services may be automated through the system 100. For example, the system 100 may include at least one sensing or image capturing device 104 configured to capture one or more images of a patient 106 in or around a medical environment (e.g., a hospital, a physician's office, a scan or treatment room, etc.). The image capturing device 104 may comprise one or more cameras digital color cameras, 3D cameras, etc.), one or more sensors (e.g., red, green and blue (RGB) sensors, depth sensors, thermal sensors, infrared (FIR) or near-infrared (NIR) sensors, radar sensors, etc.), and/or other types of sensing devices configured to detect the patient's presence and generate one or more images depicting the patient in response. Depending on the type of sensors or sensing devices used, the images generated by the imaging capture device 104 may include, for example, a photo of the patient taken by a camera, a thermal image of the patient generated by a thermal sensor, a radar image of the patient produced by a radar sensor, and/or the like. Further, although the image capturing device 104 is described herein as being configured to take a picture or image of the patient, the image capturing device 104 may also be a scanner configured to obtain images of the patient based on an existing photo or picture of the patient (e.g., a driver's license presented by the patient during check-in).

The image capturing device 104 may be configured to be installed in various locations of the medical environment such as inside a scan/treatment room, around a registration desk, in a hallway, on the medical scanner 102, etc. From the installation location, the image capturing device 104 may capture an image of the patient from a certain viewpoint or angle. The viewpoint or angle of the image capturing device 104 may be adjusted (e.g., by sending a control signal to the device or by manually adjusting the orientation of the device) so that multiple views or images of the patient may be taken from different viewpoints or angles using a single image capturing device. Alternatively, multiple image capturing devices may be included in the system 100 to capture images of the patient from different angels or viewpoints.

In example implementations, a first image capturing device (e.g., a first instance of the image capturing device 104) may be installed at a location (e.g., at a registration desk or kiosk) to capture an image of the patient upon the patient's arrival at a medical facility. The image may then be used to identify the patient, determine a medical procedure scheduled for the patient based on the identity and direct the patient to an appropriate treatment or scan room 108 for receiving the medical procedure. In example implementations, a second image capturing device (e.g., a second instance of the image capturing device 104) may be installed in the treatment or scan room 108 to capture images of the patient before and/or during a medical procedure. The images may then be used to determine at least one characteristic of the patient, to determine or verify the identity of the patient, to determine and/or adjust (e.g., automatically and/or remotely) one or more operating parameters associated with the medical procedure, and/or to monitor the activities or status of the patient before and during the medical procedure.

The system 100 may further include a control unit 110 configured to receive and process the images of the patient produced by the image capturing device 104. The control unit 110 may be located in the same room 108 as the image capturing device 104 and/or the patient 106. The control unit 110 may also be located remotely from the image capturing device 104 or the patient 106, for example, in a room 112 (e.g., a control room) that is separate or isolated from the room 108 (e.g., the rooms 108, 112 may be located on different floors or in different buildings). Regardless of its location, the control unit 110 may be communicatively coupled to the image capturing device 104, for example, over a communication network 114 (e.g., a wired or wireless communication network). In examples, the control unit 110 may be configured to retrieve or receive images from the image capturing device 104 over the communication network 114 on a periodic basis (e.g., once every of minute, according to a predetermined schedule, etc.). In examples, the control unit 110 may be configured to receive a notification from the image capturing device 104 when an image has become available and to retrieve the image from the sensing device in response to receiving the notification.

Once received or retrieved by the control unit 110, the images of the patient may be used to automate one or more aspects of a healthcare service for the patient. For example, in response to receiving the images from the image capturing device 104, the control unit 110 may analyze the images (e.g., at a pixel level such as pixel by pixel, in groups of pixels, etc.) to extract a plurality of features that collectively indicate the identity of the patient. In examples, the control unit 110 may determine the identity of the patient by comparing these extracted features against a set of known features of the patient stored in a feature database. In examples, the control unit 110 may utilize an artificial neural network trained for visual recognition to extract the features and determine the identity of the patient. The neural network may be a convolutional neural network (CNN) that comprises a cascade of layers each trained to make pattern matching decisions based on a respective level of abstraction of the visual characteristics contained in the images (e.g., in the pixels of the images). The training of the neural network may be performed using large amounts of imagery data and/or specific loss functions through which the neural network may learn to extract features in the form of feature vectors) from a newly provided input image, determine whether the features match those of a known person, and indicate the matching results at an output of the neural network. Example implementations of visual recognition and neural networks will be described in greater detail below.

In addition to the identity of the patient, the control unit 110 may also be configured to determine one or more characteristics (e.g., physical characteristics) of the patient based on the images produced by the image capturing device 104. These characteristics may include, for example, height, weight, body shape, pose, age, and/or gender of the patient that may be used to facilitate the automation of healthcare services. For example, the characteristics may be used to verify the identity of the patient against other sources of information regarding the patient. These sources of information may include, for instance, a medical record repository 116 (e.g., one or more medical record databases) configured to store patient medical information such as the patient's general information (e.g., patient ID, name, address, weight, height, age, gender, etc.), diagnostic and treatment history, imagery data associated with a past medical procedure, etc. The repository 116 may be communicatively coupled to the control unit 110 via the communication network 114 or a different communication network. As such, the control unit 110 may, in response to determining the identity and/or the characteristics of the patient based on the images acquired from the image capturing device 104, retrieve all or a subset of the patient information from the repository 116 and cross-check the retrieved patient information (e.g. height, weight, gender, age) against the characteristics of the patient determined from the images to identify potential errors in the identification.

The characteristics of the patient described herein may also be used to configure or adjust a medical procedure for the patient. For example, upon determining the identity of the patient, the control unit 110 may be further configured to determine that a certain medical procedure (e.g., a chest X-ray, a CT scan, etc.) is to be performed for the patient, and retrieve information about the medical procedure by querying scheduling and/or medical history information stored in the repository 116. The retrieved information may include operating parameters associated with the medical procedure such as scan locations, scan directions, and/or scan ranges, which may be comprised in a protocol designed for the medical procedure. Based on the parameter information and the characteristics of the patient, the control unit 110 may proceed to configure the medical equipment (e.g., the scanner 102) involved in the medical procedure. For example, the control unit 100 may determine, based on the scan location information indicated in a scan protocol and the height of the patient, that one or more adjustments (e.g., adjustments to the height of a scan bed or a scan direction) need to be made to the scanner 102, and subsequently transmit a control signal to the scanner to effectuate the adjustments. The control signal may include a di and/or analog control signal, and may be transmitted to the scanner via wired or wireless means.

The control unit 110 may determine the parameters associated with a medical procedure or a medical device based on a spatial relationship between the at least image capturing device and the medical device (e.g., a medical scanner). For example, the at least one image capturing device may be associated with or characterized by a first coordinate system, and the images produced by the at least one image capturing device may define objects captured in the images using the first coordinate system. The medical device, on the other hand, may be associated with or characterized by a second coordinate system that is different from the first coordinate system (e.g., in terms of origins and/or orientations). The control unit 110 may be configured to determine the spatial relationship between the first and second coordinate systems, and, when necessary, convert the coordinates of an object (e.g., contained in an image of the patient) in the first coordinate system to corresponding coordinates in the second coordinate system. As such, a location of the object relative to the medical device (e.g., in the second coordinate system) may be determined based on the location of the object indicated by the image capturing device (e.g., as defined in the first coordinate system). The location information may then be used to determine or adjust parameters associated with the medical procedure or the medical device (e.g., a position and/or orientation of a medical scanner). In examples, the control unit may be configured to overlay the one or more images of the patient with an indication of the parameters determined based on the spatial relationship described herein, and cause a representation of the overlaid images to be displayed to a medical professional (e.g., to facilitate medical decision making based on the images captured by the image capturing device).

The control unit 110 may use the images provided by the image capturing device 104 to monitor the status of the patient before and during a medical procedure. For example, the control unit 110 may be configured to evaluate the readiness of the patient by collecting multiple images of the patient over a certain period of time, extracting positional information of the patient from each of the collected images, and comparing the positional information in the multiple images to ensure that the patient has remained steady in a desirable position or pose for the medical procedure. In another example, the control unit 110 may be configured to recognize activities of the patient by analyzing multiple images collected by the image capturing device 104 to determine whether the patient has followed instructions (e.g., positioning instructions) provided to the patient.

Information and/or instructions generated by the control unit 110 may be presented to the patient 106 in various forms. In an example implementation, the system 100 may include a display device 118 located in the treatment room 108. The display device 118 may include one or more monitors (e.g., computer monitors, TV monitors, tablets, mobile devices such as smart phones, etc.), one or more speakers, one or more augmented reality (AR) devices (e.g., AR goggles), and/or other accessories configured to facilitate audio or visual representation. The display device 118 may be communicatively coupled to the control unit 110 via the communication network 114 or another suitable communication link. As described herein, the information or instructions presented via the display device 118 may include desired positions and poses for an upcoming medical procedure, positions taken by the patient during past scans, adjustment instructions for the patient to get into the desired positions or poses, etc. The information and/or instructions may be presented to the patient 106 in various formats including, for example, videos, animations, AR presentations, etc.

Information and/or instructions generated by the control unit 110 may also be presented (e.g., remotely) to a medical professional overseeing the patient or the medical procedure. The medical professional may be located remotely from (e.g., isolated from) the patient 106, e.g., in the room 112. The information presented to the medical professional may include the images captured by the at least one image capturing device, feedback information regarding the current position or pose of the patient 106, a medical history of the patient 106, the current operating parameters or state of the medical scanner 102, etc. In examples, the feedback may include information (e.g., patient position information) synthesized by the control unit 110 based on images captured from multiple viewpoints or angles (e.g., by multiple instances of the image capturing device 104). The medical professional may use the multi-view information to visually inspect to the patient and/or the medical equipment in room 108 to ensure that the patient and equipment are indeed ready for an upcoming procedure. The information described herein may be presented via a display device attached to the control unit 110 or via a separate display device (not shown in FIG. 1) isolated from the patient (e.g., in a separate room from where the patient is). The display device may include one or more monitors (e.g., computer monitors, TV monitors, tablets, mobile devices such as smart phones, etc.), one or more speakers, one or more augmented reality (AR) devices (e.g., AR goggles), and/or other accessories configured to facilitate audio or visual representation. The display device may be communicatively coupled to the control unit 110 via the communication network 114 or another suitable communication link. The information and/or instructions may be presented to the medical professional in various formats including, for example, videos, animations, AR presentations, etc.

The system 100 may also include devices for a medical professional to provide inputs or instructions to the system 100 or the patient 106. Such inputs or instructions may relate to adjusting the position of the patient or the operating parameters of scanner 102, confirming the readiness of the patient or the scanner, initiating a medical procedure after the readiness is confirmed, etc. Suitable input devices for accomplishing these tasks may include a keyboard, a mouse, a voice-controlled input device, a touch sensitive input device (e.g., a touch screen), and/or the like. The input devices may be attached to the control unit 110 or may be separate from the control unit 110.

In example implementations, the control unit 110 may also be configured to make automatic diagnosis for the patient 106 based on information collected during the medical procedure (e.g., based on scan images of the patient collected during the procedure), physical characteristics of the patient and/or a medical history of the patient. For example, the control unit 110 may utilize artificial intelligence (e.g., a neural network trained for medical image recognition) to identify abnormalities in the scan images of the patient and the medical conditions that may be indicated by the abnormalities. The control unit 110 may further prioritize and/or label each scan image or diagnostic finding as critical, urgent, non-urgent, normal or uncertain, and generate a report for the diagnoses and/or prioritization. The control unit 110 may provide the report to a medical professional for further analysis or investigation. The control unit 110 may also provide additional instructions to the patient 106 based on the diagnoses. For example, the control unit 110 may instruct the patient to leave the treatment room 108 if the diagnosis is negative or to schedule additional procedures if the diagnosis is ambiguous or positive. Example implementations of AI-based medical diagnosis will be described in greater detail below.

Using the system 100, a healthcare service provider may be able to monitor and control multiple treatment or scan rooms (e.g., the room 108) simultaneously, e.g., from one control room (e.g., the room 112). The control room may host a control unit (e.g., the control unit 110) communicatively coupled to multiple image capturing devices (e.g., the image capturing device 104) and configured to receive images provided by the image capturing devices. Based on the images, the control unit may be able to carry out multiple operations associated with automating a healthcare service (e.g., patient identification/verification, patient readiness detection, patient positioning, etc.). One or more of these operations may be performed by the control unit in parallel, and feedback may be provided to a medical professional to ensure the operations proceed in a desired manner (e.g., the medical professional may intervene in the automated process if necessary).

It should be noted that one or more of the operations or tasks described herein as being executed by the control unit 110 may also be performed by another device or component of the system 100 such as the image capturing device 104. For example, the image capturing device 104 may be configured with the necessary computing power or logic for determining the identity or characteristics of the patient, or adjusting the operating parameters (e.g., the height of a scan bed) of a medical device.

Figure 2:
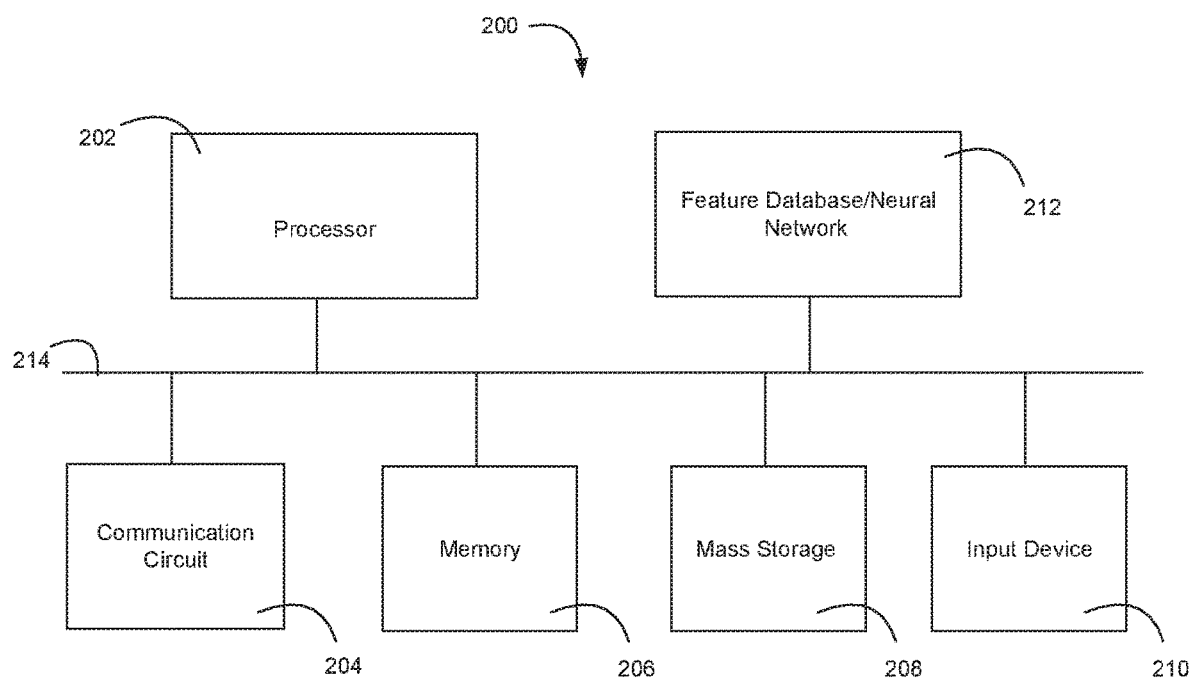
FIG. 2 is a simplified block diagram illustrating an example control unit as described herein.

FIG. 2 is a simplified block diagram illustrating an example control unit 200 (e.g., the control unit 110 in FIG. 1) as described herein. The control unit 200 may operate as a standalone device or may comprise multiple interconnected (e.g., networked or clustered) devices configured to jointly perform the functions described herein. In examples of a networked deployment, the control unit 200 may operate in the capacity of a server device or a client device, or it may act as a peer device in peer-to-peer (or distributed) network environments. Further, while only a single unit is shown in FIG. 2, the term "control unit" shall be taken to potentially include multiple units or machines that individually or jointly execute a set of instructions to perform any one or more of the functions discussed herein. The multiple units or machines may be hosted in one location or multiple locations, for example, under a distributed computing architecture.

The control unit 200 may include at least one processor 202 which in turn may include one or more of a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The control unit 200 may further include a communication circuit 204, a memory 206, a mass storage device 208 and/or an input device 210 interconnected with each other and the processor 202 via a communication link 214 (e.g., an address and/or data bus). The communication circuit 204 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 206 may include a machine-readable medium configured to store instructions that, when executed, cause the processor 202 to perform one or more of the functions described herein. Examples of a machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 208 may include one or more magnetic disks such as internal hard disks, removable disks, magneto-optical disks, CD-ROM or DVD-ROM disks, etc., on which instructions and/or data may be stored to facilitate the performance of the functions described herein. The input device 210 may include a keyboard, a mouse, a voice-controlled input device, a touch sensitive input device (e.g., a touch screen), and/or the like for receiving user inputs (e.g., from a medical professional) to the control unit 200.

The processor 202 may be configured to perform various tasks associated with automating a medical procedure for a patient. These tasks may include, for example, determining the characteristics and/or identity of a patient based on images generated by an image capturing device (e.g., the image capturing device 104 in FIG. 1), retrieving medical information of the patient from one or more medical record repositories (e.g., the repository 116 in FIG. 1), providing positioning assistance to the patient based on physical attributes of the patient reflected in the received images, making autonomous diagnosis and/or treatment planning for the patient based on past and present information gathered about the patient, interacting with the patient or medical professionals during the medical procedure to ensure all parties involved are properly informed, etc.

One or more of the aforementioned tasks may be accomplished utilizing artificial intelligence techniques such as machine learned decision models and AI-based imaging processing techniques. In a first aspect, the processor 202 may be configured to process received images through a preprocessing stage during which the processor may discard images that are of poor quality and/or convert qualified images into a suitable format for further processing. The processor 202 may also prepare the images in ways that would reduce the complexity of further processing. Such preparation may include, for example, converting color images to grayscale, resize the images into unified dimensions, and/or the like.

In a second aspect, the processor 202 may include or may be coupled to a feature database 212 configured to store visual representations of known features of a patient (e.g., facial features, body shapes, positions, poses, walking patterns, etc.) and/or known patterns (e.g., X-ray or CT scan patterns) that indicate certain medical conditions. The known features or patterns may be pre-computed and stored in the feature database 212 based on imagery data collected from various sources including, for example, pictures taken during the patient's past visits to a medical facility and/or historical medical records stored in a repository (e.g., the repository 116 shown in FIG. 1). The feature database 212 may be communicatively coupled to the processor 202 and used by the processor for identifying a patient or making a diagnosis. For example, in response to receiving images of a patient from the image capturing device 104, the processor 202 may analyze the images (e.g., at a pixel level) to extract a set features present in the images. The features may relate to a variety of attributes of the patient including but not limited to body contours, facial features, walking patterns, poses, etc. Each feature may correspond a combination of structures (e.g., points, edges, objects, etc.) arranged in a specific manner in the images, and as such may be identified based on the presence of one or more keypoints. These keypoints may include but are not limited to, for example, points at which the direction of the boundary of an object changes abruptly, intersection points between two or more edge segments, etc. The keypoints may be characterized by well-defined positions in the image space and/or stability to illumination/brightness perturbations. Accordingly, the keypoints may be identified based on image derivatives, edge detection, curvature analysis, and/or the like. And once identified, the keypoints and/or the feature represented by the keypoints may be described with a feature descriptor or feature vector. In an example implementation of such feature descriptors or vectors, information related to the feature (e.g., appearance of the local neighborhood of each keypoint) may be represented by (e.g., encoded into) a series of numerical values stored in the feature descriptor or vector. The descriptor or vector may then be used as a "fingerprint" for differentiating one feature from another or matching one feature with another.

In a third aspect, the processor 202 may include, be coupled to, or otherwise utilize a machine learning model (e.g., in addition to or instead of the feature database) configured to perform one or more of the tasks described herein. In an example implementation, the machine learning model may be based on or acquired through a neural network 212 (e.g., in addition to or instead of the feature database). The neural network 212 may include a convolutional neural network (CNN) and/or a deep neural network (DNN) that comprises multiple layers (e.g., an input layer, one or more convolutional layers, one or more non-linear activation layers, one or more pooling layers, one or more fully connected layers, and/or an output layer). Each of the layers may correspond to a plurality of filters (or kernels), and each filter may be designed to detect a specific type of visual features or patterns. The filters may be associated with respective weights that, when applied to an input, produce an output indicating whether certain visual features or patterns have been detected. The weights associated with the filters may be learned by the neural network 212 through a training process that comprises inputting a large number of images from a training dataset to the neural network (e.g., in a forward pass), calculating losses resulting from the weights currently assigned to the filters (e.g., based on a loss function such as a margin based loss function), and updating (e.g., in a backward pass) the weights assigned to the filters so as to minimize the losses (e.g., based on stochastic gradient descent). Once trained, the neural network 212 may be able to take an image at the input layer, extract and/or classify visual features or patterns from the image, and provide an indication at the output layer for whether the input image matches that of a known person or a known scan pattern associated with a medical condition.

Figure 3:
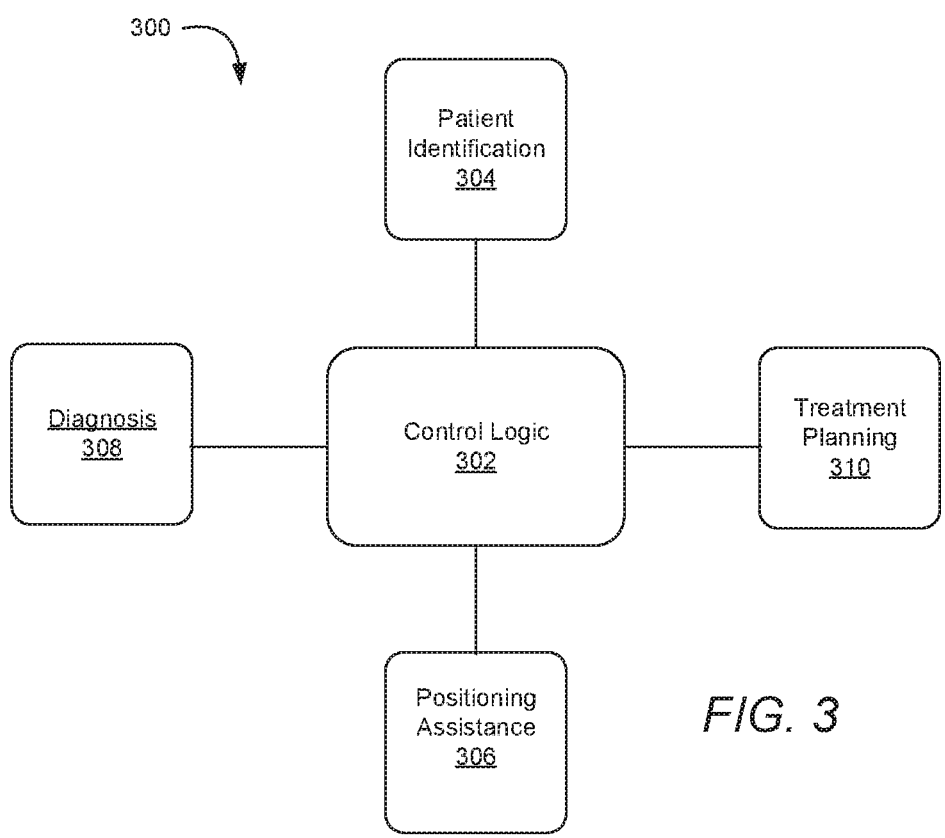
FIG. 3 is a simplified block diagram illustrating functional modules of an example control unit as described herein.

FIG. 3 is a simplified diagram illustrating example functional modules that may be comprised in a processor 300 (e.g., the processor 202) in accordance with examples provided herein. It should be noted that, when referenced herein, the term "module" does not mean or imply that functionalities described in association with the module are implemented separately from or independently of other functionalities of the processor 300. Rather, the term is merely used for the convenience of description and not meant to indicate any structural limitations or design preferences.

As shown in FIG. 3, the processor 300 may include a control logic module 302, a patient identification module 304, a positioning assistance module 306, a diagnosis module 308, and/or a treatment planning module 310. The control logic module 302 may be responsible for controlling the general operation of the processor 300 such as receiving or responding to user inputs, while the other modules may be configured to perform specific functions relating to the automation of healthcare services as described herein. For example, the patient identification module 304 may be configured to receive images generated by an image capturing device (e.g., the image capturing device 104) and extract features from the images to determine the identity and/or characteristics (e.g., physical characteristics) of the patient, e.g., using one or more of the AI-based on image recognition techniques described herein.

The positioning assistance module 304 may be responsible for monitoring the position of the patient during a medical procedure and providing guidance to the patient so as to help the patient get into a desired position or pose. Such desired position or pose may be determined, for example, based on a protocol associated with the medical procedure and/or physical characteristics of the patient determined from the images acquired by the image capturing device 104. For example, the positioning assistance module 304 may determine, based on a patient identity provided by the patient identification module 304, that a scan procedure is to be performed for the patient and that the scan location is in the chest area of the patient. The positioning assistance module 304 may further determine the height of the patient based on one or more images acquired by the image capturing device 104. Combining these pieces of information, the positioning assistance module 304 may determine and instruct the patient about a proper position or pose to take so that the scan can be accurately performed in the chest area of the patient. In the process, the positioning assistance module 304 may also generate control signals for adjusting one or more operating parameters of the medical scanner (e.g., the height of a scan bed, the orientation of a scanner, etc.) to help the patient get into the desired position. The control signals may be digital and/or analog control signals and may be transmitted to the medical scanner via wired or wireless means.

The positioning assistance module 304 may also be responsible for evaluating the readiness of a patient during a medical procedure. For instance, after the patient has been instructed about a desirable position to take, the positioning assistance module 304 may further determine, based on multiple images of the patient taken after the instructions have been given, that the patient has entered into and remained steady in the desired position. The positioning assistance module 304 may then initiate the medical procedure or inform a medical professional that the patient is ready for the procedure.

The diagnosis module 308 may be responsible for making automatic diagnoses for a patient (e.g., as part of initial screening) based on information collected during a medical procedure (e.g., based on one or more scan images of the patient). The automatic diagnosis may be made, for example, utilizing one or more of the AI-based image recognition techniques described herein to identify abnormalities in the scan images and determine the medical conditions that may be associated with the abnormalities. Upon obtaining the diagnostic results, the diagnosis module 308 may prioritize or indicate the results as critical, urgent, non-urgent, normal or uncertain, and report the results to a medical professional for analysis or review.

The treatment planning module 310 may be responsible for devising treatment plans for a patient based on machine-learned treatment strategies and information collected about the patient. The treatment strategies (or models) may be learned (e.g., using a neural network) from databases of clinically accepted plans, for example, by using geometric and dosimetric features contained in the plans to predict a range of achievable dose deposition for new patients. The information collected about the patient may include physical characteristics (e.g., body shape, weight, etc.) of the patient, medical history of the patient, and/or diagnoses of the patient. As described herein, the physical characteristics of the patient may be determined based on images acquired by the image capturing device 104, the medical history of the patient may be retrieved from a medical record repository such as the repository 116, and the diagnoses of the patient may be obtained from the diagnosis module 308. Once collected, one or more pieces of the information may be provided as inputs to the machine-learned treatment models (e.g., to a neural network) to derive a suitable plan for the patient at the output of the model (e.g., the neural network).

Figure 4:
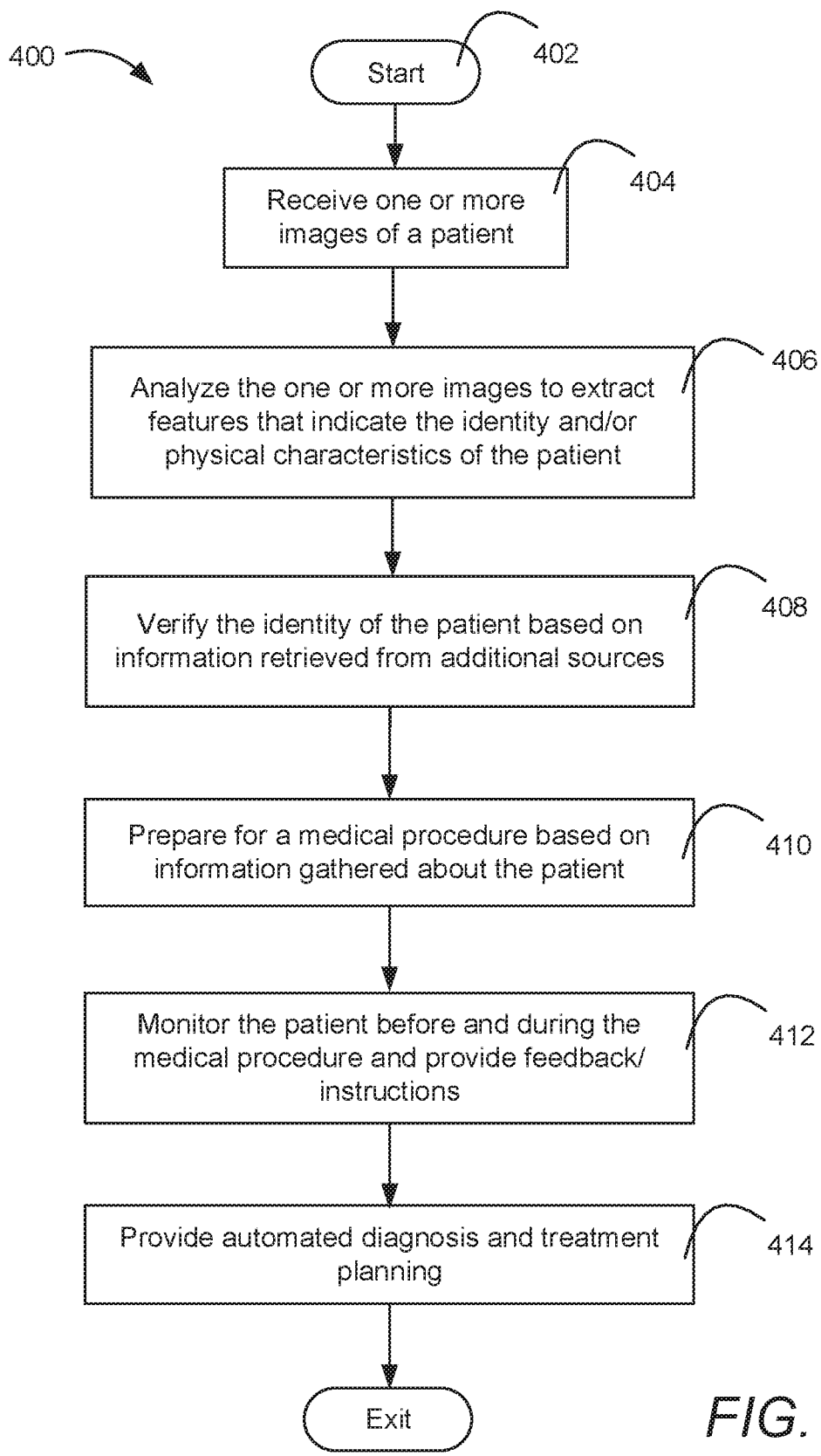
FIG. 4 is a flow diagram illustrating a method that may be implemented by the automated healthcare system depicted in FIG. 1.

FIG. 4 is a flow diagram illustrating a method 400 that may be implemented by an automated healthcare system described herein (e.g., the system 100 of FIG. 1). For simplicity of explanation, the operations in the method 400 are depicted and described herein with a specific order. It should be appreciated, however, that these operations may occur in various orders and/or concurrently, and with other operations not presented and described herein. Furthermore, not all illustrated operations may be required to implement the method disclosed herein.

The method 400 may be started by a control unit of the automated healthcare system (e.g., the control unit 110 or 200 shown in FIG. 1 or FIG. 2) at 402. At 404, the control unit may receive one or more images of a patient from an image capturing device (e.g., the image capturing device 104 of FIG. 1) located in or around a medical facility such as a hospital, a physician's office, a scan or treatment room, etc. The images may be in a variety of formats including camera photos, thermal images, radar images, and/or the other types of imagery that contain a representation of the patient. At 406, the control unit may analyze the received images and extract features (or patterns) from the images that collectively indicate the identity and/or characteristics (e.g., body shape, height, etc.) of the patient. The analysis of the images may be conducted at a pixel level (e.g., pixel by pixel, by groups of pixels, etc.) and/or utilizing a neural network or feature database. Once extracted, the features may be compared with known features of patients to determine whether a match can be found. If a match is found, the control unit may, at 408, further verify the identity of the patient based on other information the control unit can gather about the patient. For instance, using the identity determined from the images, the control unit may retrieve additional information regarding the patient from a record repository. The additional information may include, for example, height, weight, body shape, age, and/or gender of the patient. The control unit may compare the additional information with the physical characteristics of the patient determined from the images and determine whether there is any error in the identification of the patient.

At 410, the control unit may start preparing the patient for an upcoming medical procedure. For example, the control unit may determine, based on the characteristics (e.g., physical characteristics) of the patient identified from the images and/or a protocol designed for the medical procedure, a desired patient position for the medical procedure and/or an operating parameter of the medical equipment involved in the procedure. Subsequently, the control unit may instruct the patient (e.g., by sending visual and/or audio instructions to the patient) about the desired position and/or ways to maneuver into the desired position. The control unit may also generate and transmit control signals to the medical equipment (e.g., to a controller of the medical equipment) to effectuate the operating parameter (e.g., the height of a scan bed) needed for the medical procedure. The control signals may be digital and/or analog control signals and may be transmitted to the medical equipment via wired or wireless means.

At 412, the control unit may monitor the status and/or movements of the patient before and during the medical procedure. For example, the control unit may determine the readiness of the patient for the medical procedure by analyzing multiple images of the patient gathered over a time period during the preparation process. The control unit may extract positional information of the patient from each of the images and compare the positional information across multiple images to ensure that the patient has remained steady in a desired position for the medical procedure. Similarly, the control unit may identify movements of the patient by analyzing multiple images of the patient collected during the medical procedure to ensure that the patient has followed instructions (e.g., positioning instructions) provided by the control unit or a medical professional overseeing the medical procedure. The control unit may provide feedback regarding the patient's status and/or movements to the medical professional. The control unit may also provide instructions to the patient to assist the patient before and during the medical procedure.

At 414, the control unit may provide automated diagnosis and/or treatment planning for the patient, for example, utilizing AI-based prediction models and/or methods described herein.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "segmenting", "analyzing", "determining", "enabling", "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A system for providing automated healthcare services, comprising:
   at least one image capturing device configured to capture one or more images of a patient; and
   one or more processors configured to:
   receive the one or more images of the patient generated by the at least one image capturing device;

determine, using an artificial neural network (ANN), an identity of the patient, wherein the ANN comprises a plurality of convolutional layers and is trained to extract a plurality of features from the one or more images of the patient by processing the one or more images through the plurality of convolutional layers, and wherein the identity of the patient is determined based on the plurality of features extracted from the one or more images of the patient;

complete, automatically, one or more aspects of a medical procedure for the patient based on the identity of the patient determined using the ANN, wherein the one or more aspects of the medical procedure that are automatically completed include remotely adjusting an operating parameter of a medical device associated with the medical procedure or remotely providing positioning instructions regarding the medical procedure to the patient; and provide feedback regarding the patient or the medical procedure to a receiving device isolated from the patient.

2. The system of claim 1, wherein the at least one image capturing device comprises a digital camera or a thermal sensor, and the one or more images of the patient comprise a photo of the patient taken by the digital camera or a thermal image of the patient generated by the thermal sensor.

3. The system of claim 1, wherein remotely adjusting the operating parameter of the medical device comprises:
retrieving, based on the identity of the patient, a medical history of the patient related to the medical procedure;
determining the operating parameter of the medical device based on the medical history of the patient; and
transmitting a control signal to the medical device to adjust the operating parameter of the medical device.

4. The system of claim 3, wherein the medical device comprises a medical scanner, the operating parameter of the medical device that is adjusted comprises at least one of a scan location, a scan direction or a scan range of the medical scanner, and a value of the operating parameter is indicated in the retrieved medical history of the patient.

5. The system of claim 1, wherein remotely providing positioning instructions regarding the medical procedure to the patient comprises determining, based on the plurality of features extracted by the ANN from the one or more images of the patient, a position of the patient relative to the medical device and instructing the patient to maintain or adjust the position for the medical procedure.

6. The system of claim 1, wherein remotely providing positioning instructions regarding the medical procedure to the patient comprises:
determining a spatial relationship between the at least one image capturing device and the medical device;
retrieving, based on the identity of the patient, a medical history a treatment plan of the patient;
determining a target scan area of the patient based on the medical history or the treatment plan of the patient;
identifying, based on the plurality of features extracted by the ANN from the one or more images of the patient, the target scan area in the one or more images;
determining, based on the spatial relationship between the at least one image capturing device and the medical device, a location of the target scan area relative to the medical device; and
providing the positioning instructions based on the location of the target scan area relative to the medical device.

7. The system of claim 6, wherein the at least one image capturing device is associated with a first coordinate system, the medical device is associated with a second coordinate system, identifying the target scan area in the one or more images based on the plurality of features extracted by the ANN comprises determining coordinates of the target scan area in the first coordinate system based on the plurality of features extracted by the ANN, and determining the location of the target scan area relative to the medical device comprises converting the coordinates of the target scan area in the first coordinate system to coordinates of the target scan area in the second coordinate system.

8. The system of claim 6, wherein the one or more processors are configured to determine the operating parameter of the medical device based on the location of the target scan area and the spatial relationship between the at least one image capturing device and the medical device, the one or more processors further configured to overlay the one or more images of the patient with an indication of the operating parameter and cause a representation of the overlaid one or more images to be displayed on the receiving device.

9. The system of claim 1, wherein the one or more aspects of the medical procedure are automatically completed for the patient without requiring a medical professional to make physical contact with the patient.

10. The system of claim 1, wherein the receiving device is located in a separate room from the patient and wherein the feedback regarding the patient or the medical procedure is provided to the receiving device over a wired or wireless communication network.

11. The system of claim 1, wherein the one or more processors are further is configured to:
determine, based on the identity of the patient, a desired position of the patient for the medical procedure;
determine, based on the plurality of features extracted by the ANN from the one or more images of the patient, a current position of the patient; and
determine whether the patient is in a ready position for the medical procedure based on the desired position and the current position of the patient.

12. The system of claim 11, wherein the one or more processors are configured to acquire multiple images of the patient over a period of time, determine a respective position of the patient in each of the multiple images based on the plurality features extracted by the ANN from the multiple images, and determine whether the patient has remained steady over the period of time by comparing the respective position of the patient in each of the multiple images.

13. The system of claim 12, wherein the instructions are remotely provided to the patient in response to determining that the patient has not remained steady over the period of time and wherein the instructions comprise a command for the patient to remain steady.

14. The system of claim 11, wherein the system comprises multiple image capturing devices each configured to capture an image of the patient from a respective angle, and wherein the one or more processors are configured to determine the current position of the patient based on the respective images of patient captured by the multiple image capturing devices.

15. The system of claim 1, wherein the one or more processors are configured to determine the identity of the patient by comparing the plurality of features extracted by the ANN from the one or more images of the patient with known features of the patient.

16. The system of claim 15, further comprising a database configured to store the known features of the patient.

17. The system of claim 1, wherein the plurality of convolutional layers of the ANN are associated with respective weights for extracting the plurality of features from the one or more images of the patient, and wherein the weights are learned in a training process that comprises:
  providing a training image to the ANN;
  causing the ANN to extract, using preliminary values of the respective weights associated with the plurality of convolutional layers, features from the training image;
  determining, based on a loss function, a loss associated with the extraction; and
  updating the preliminary values of the respective weights associated with the plurality of convolutional layers to reduce the loss.

18. The system of claim 1, wherein the plurality of features extracted by the ANN from the one or more images of the patient is indicative of at least one of a body shape of the patient, a facial feature of the patient, or a walking pattern of the patient.

19. A device for providing automated healthcare services, comprising:
  at least one processor configured to:
    receive one or more images of a patient generated by an image capturing device;
    determine, using an artificial neural network (ANN), an identity of the patient, wherein the ANN comprises a plurality of convolutional layers and is trained to extract features from the one or more images of the patient by processing the one or more images through the plurality of convolutional layers, and wherein the identity of the patient is determined based on the plurality of features extracted from the one or more images of the patient;
    complete, automatically, one or more aspects of a medical procedure for the patient based on the identity of the patient determined using the ANN, wherein the one or more aspects of the medical procedure that are automatically completed include remotely adjusting an operating parameter of a medical device associated with the medical procedure or remotely providing positioning instructions regarding the medical procedure to the patient; and
    provide feedback regarding the patient or the medical procedure to a receiving device isolated from the patient.

20. A method for providing automated healthcare services, the method comprising:
  receiving one or more images of a patient generated by an image capturing device;
  determining, using an artificial neural network (ANN), an identity of the patient, wherein the ANN comprises a plurality of convolutional layers and is trained to extract features from the one or more images of the patient by processing the one or more images through the plurality of convolutional layers, and wherein the identity of the patient is determined based on the plurality of features extracted from the one or more images of the patient;
  completing, automatically, one or more aspects of a medical procedure for the patient based on the identity of the patient determined using the ANN, wherein the one or more aspects of the medical procedure that are automatically completed for the patient include remotely adjusting an operating parameter of a medical device associated with the medical procedure or remotely providing positioning instructions regarding the medical procedure to the patient; and
  providing feedback regarding the patient or the medical procedure to a receiving device isolated from the patient.

* * * * *